(12) United States Patent
Tamura et al.

(10) Patent No.: US 8,309,298 B2
(45) Date of Patent: Nov. 13, 2012

(54) METHOD FOR DETECTING PROTEIN

(75) Inventors: Shigeyuki Tamura, Hyogo (JP);
Tomokazu Yoshida, Hyogo (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 11/527,584

(22) Filed: Sep. 27, 2006

(65) Prior Publication Data

US 2007/0105177 A1    May 10, 2007

(30) Foreign Application Priority Data

Sep. 27, 2005  (JP) .................................. 2005-280463
Feb. 28, 2006  (JP) .................................. 2006-051909

(51) Int. Cl.
*C12Q 1/00* (2006.01)
(52) U.S. Cl. ............................................. 435/4
(58) Field of Classification Search ................ 435/4
See application file for complete search history.

(56) References Cited

U.S. PATENT DOCUMENTS 6,255,485 B1     7/2001  Gray et al.
2002/0164673 A1 * 11/2002  Ishihara et al. ................. 435/15

FOREIGN PATENT DOCUMENTS

EP           1 233 060 A2    2/2002
WO    WO 2007/141030     * 12/2007

OTHER PUBLICATIONS

Martin et al, "Simultaneous trichromatic fluorescence detection of proteins on Western blots using an alkaline phosphatase- and horseradish peroxidase-antibody conjugates" Proteomics, vol. 3, No. 7, Jul. 2003, pp. 1215-1227, pp. 1215-1227, XP002411412.
Kelly et al, "Isolation of a colon tumor specific binding peptide using phage display selection", Neoplasia (New York), vol. 5, No. 5, Oct. 2003, pp. 437-444, XP002411411.
Ishihara et al, "A new cancer diagnostic system based on a CDK profiling technology", Biochimica et Biophysica Acta. Molecular Basis of Disease, Amsterdam, NL, vol. 1741, No. 3, Sep. 25, 2005, pp. 226-233, XP005088400.

* cited by examiner

*Primary Examiner* — Ralph Gitomer
(74) *Attorney, Agent, or Firm* — Sughrue Mion, PLLC

(57) ABSTRACT

A method for detecting an analyte in a sample is described herein. The method comprises: preparing a complex immobilized solid phase comprising a solid phase and a complex on the solid phase; the complex comprising an analyte and a signal emitting substance; treating the complex immobilized solid phase with a blocking agent; and detecting the analyte based on a signal emitted from the signal emitting substance of the complex immobilized solid phase.

12 Claims, 13 Drawing Sheets

METHOD FOR DETECTING PROTEIN

TECHNICAL FIELD

The present invention relates to a method for detecting an analyte contained in a sample, a method for quantifying activity of an enzyme, and a method for quantifying a protein in a sample.

BACKGROUND

Heretofore, the method described in US Patent publication 2002-0164673 has been known as a method for detecting an analyte in a test sample. In the US Patent publication 2002-0164673, it is disclosed that a substrate (analyte) phosphorylated with cyclin-dependent kinase (CDK) is quantified to calculate activity of the CDK. According to the US Patent publication No. 2002-0164673, in the manner specified, first, a thiophosphate group is introduced into a CDK substrate by means of CDK and adenosine 5'-O-(3-thiotriphosphate) (ATPγS); then, a fluorescent substance is combined with the substrate into which the thiophosphate group is introduced, and the resulting product is immobilized on a solid phase. Thereafter, an excitation light is irradiated on the solid phase to detect the fluorescence produced from the fluorescent substance combined with the substrate, and the phosphorylated substrate is quantified based on the detection result.

In case of detecting fluorescence, the fluorescence emitted from the fluorescent substance adsorbed nonspecifically onto the solid phase is detected as the background. For this reason, the solid phase is washed with a buffer solution after being fluorescence-labeled in the above-described manner, whereby the fluorescent substance adsorbed nonspecifically is removed to reduce the fluorescent background. As a result, the substrate immobilized on the solid support can be exactly quantified, and in addition, the activity of CDK can be correctly measured on the basis of the quantified result.

By the above-described method, however, it is required to set up strictly the washing conditions such as a washing period of time etc.

SUMMARY

The scope of the present invention is defined solely by the appended claims, and is not affected to any degree by the statements within this summary.

An aspect of the present invention relates to a method for detecting an analyte in a sample, comprising steps of:

preparing a complex immobilized solid phase comprising a solid phase and a complex on the solid phase; the complex comprising an analyte and a signal emitting substance;

treating the complex immobilized solid phase with a blocking agent; and detecting the analyte based on a signal emitted from the signal emitting substance of the complex immobilized solid phase.

DESCRIPTION OF THE PREFERRED EMBODIMENTS

Figure 1:
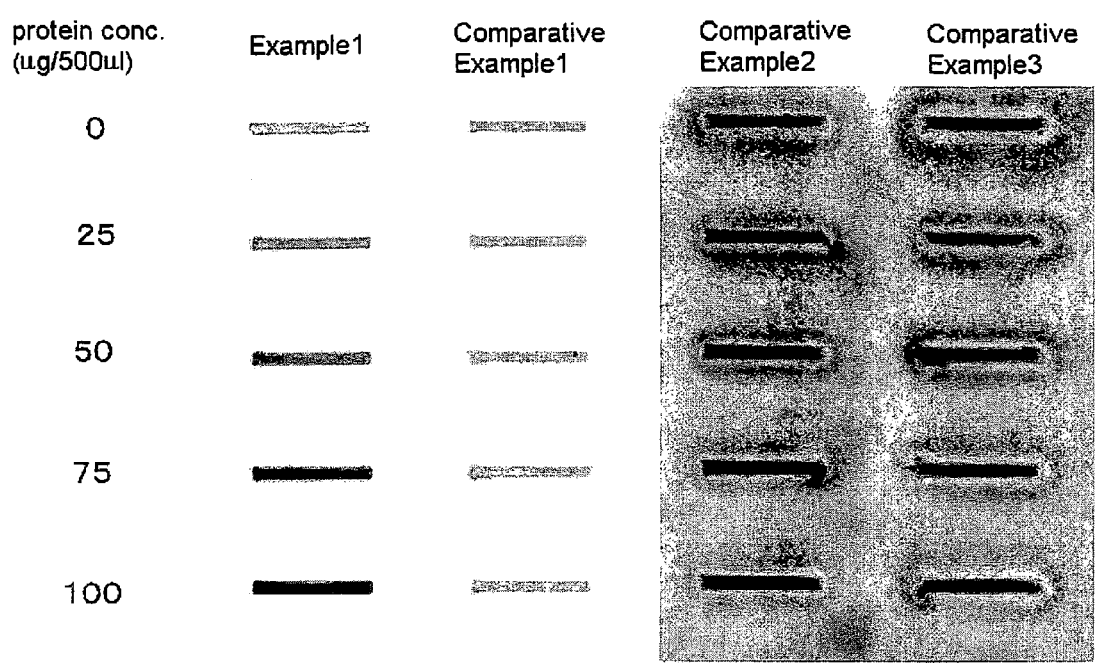
FIG. 1 shows a photograph of PVDF membrane of Example 1, Comparative example 1, Comparative example 2, and Comparative example 3.

A method for detecting an analyte in a sample as an embodiment of the present invention comprises:

preparing a complex immobilized solid phase comprising a solid phase and a complex on the solid phase; the complex comprising an analyte and a signal emitting substance;

treating the complex immobilized solid phase with a blocking agent; and detecting the analyte based on a signal emitted from the signal emitting substance of the complex immobilized solid phase.

It is to be noted that the expression "to detect an analyte" in the present specification means not only to decide qualitatively the presence of the analyte in a sample, but also to quantify the analyte.

A manner for preparing a complex immobilized solid phase is not specifically limited, but it is preferred that a signal emitting substance capable of combining with an analyte is added to a sample containing the analyte; the signal emitting substance is allowed to combine with the analyte thereby to produce the complex; and the complex is immobilized onto a solid phase. This solid phase on which the complex immobilized is herein called a complex immobilized solid phase.

Furthermore, it may be applied such a manner that either of the analyte and the signal emitting substance has been previously immobilized onto the solid phase; and the other is further immobilized, whereby a combination reaction of the signal emitting substance and the analyte is conducted on the solid phase. In other words, the combination reaction of the signal emitting substance and the analyte may be carried out either in the sample, or on the solid phase.

An analyte is not specifically limited, but it may be proteins, nucleic acids, hormones, poisonous materials and the like, wherein proteins are preferable. As a manner for immobilizing a protein onto a solid phase, a well-known blotting method is applicable wherein a commercially available blotting membrane may be used as the solid phase. An example of a material of the membrane includes polyvinylidene fluoride (PVDF), nitrocellulose, nylon (e.g. a modified nylon into which an amino group which may contain a carboxyl group or an alkyl group as the substituent is introduced), cellulose acetate and the like.

A signal emitting substance is not specifically limited, but a substance, which emits fluorescence by irradiating a light having a specified wavelength (excitation light) thereon (hereinafter, this substance is referred to as "fluorescent substance"), is preferred. An example of the fluorescent substance includes fluorescein isothiocyanate, fluorescein, Oregon Green, coumarin, eosin, phenanthroline, pyrene, Rhodamine and the like.

It is preferred that an analyte contains a functional group capable of combining specifically with a signal emitting substance. For instance, in the case where the signal emitting substance is a protein containing a thiol group, a signal emitting substance, which can combine with the thiol group, may be used. A specific example of such signal emitting substances includes 5-iodoacetamide fluorescein (5IAF), Oregon Green iodoactamide (OGI), iodoacetyl-fluorescein isothiocyanate, 5-(bromomethyl)fluorescein, fluorescein-5-maleimide, 6-iodoacetamide fluorescein, 4-bromomethyl-7-methoxycumarin, eosin-5-iodoacetamide, eosin-5-maleimide, eosin-5-iodoacetamide, N-(1,10-phenanthlorin-5-yl) bromoacetamide, 1-pyrenebutylylchloride, N-(1-pyreneethyl)iodoacetamide, N-(1-pyrenemethyl)iodoacetamide, (1-pyrenemethyl)iodoacetate, Rhodamine Red C2 maleimide and the like.

In the case where an analyte does not contain such a functional group as described above, the functional group is introduced into the analyte, whereby a signal emitting substance can be combined with the analyte. For instance, when the analyte is a protein containing no thiol group, a kinase acting on the protein as its substrate and adenosine-5'-O-(3-thiotriphosphate) (hereinafter referred to as "ATPγS") are used to introduce a thiophosphate group into the protein. As a result, the analyte may be combined with such signal emitting substance as mentioned above.

A blocking treatment is further conducted on the complex immobilized solid phase. The term "blocking treatment" means the treatment by which a blocking agent is immobilized to the solid phase. It is preferred to stop the conjugation reaction of an analyte with a signal emitting substance prior to the blocking treatment. For the sake of stopping the combination reaction, a reducing agent having a thiol group may be used. When the reducing agent containing a thiol group is added as a reaction-stopping agent during the conjugation reaction of the analyte and the signal emitting substance, the conjugation reaction is stopped. An example of the reducing agent containing a thiol group includes 2-mercaptoethanol, D-type cysteine, L-type cysteine, acetylcysteine, 2-mercaptopropionic acid, mercaptoacetic acid, 2-aminoethanethiol, dithiothreitol, glutathione, dodecanethiol and the like wherein they may be used alone or in the combinations thereof.

An example of the blocking agent used for a blocking treatment includes albumin, casein, globulin, gelatin and the like wherein they may be used alone or in the combinations thereof. In case of albumin, it is not specified that the albumin is derived from which kind of animals such as bovine, goat, rabbit, and human. It is preferred to use BSA as the albumin. The blocking treatment may be conducted either once, or divided in plural times.

In case of immobilizing a blocking agent onto a solid phase, it is preferred to use a blocking solution in a condition wherein the blocking agent is dissolved. In the blocking solution, a buffering agent may be contained. An example of the buffering agent includes a tris-hydrochloric acid buffering agent, an imidazole-acetic acid buffering agent, a phosphoric acid buffering agent, a citric acid buffering agent, a malic acid buffering agent, an oxalic acid buffering agent, a phthalic acid buffering agent, a glycine buffering agent, an acetic acid buffering agent, a succinic acid buffering agent, a boric acid buffering agent, a carbonic acid buffering agent, a Good's buffering agent and the like.

After immobilizing a blocking agent to a solid phase, a signal is detected. A manner for detecting the signal depends on the type of a signal emitting substance. For instance, when a signal emitting substance contains a fluorescent substance, an excitation light is irradiated to the solid phase to excite fluorescence, so that the signal may be detected by means of a fluorescence analyzer and the like. In case of quantifying an analyte, an amount of the analyte can be calculated based on the intensity of the detected signal. In the case of quantifying an analyte, it is preferred to apply a calibration curve. The calibration curve may be obtained by such a manner that a known amount of a protein with which a signal emitting substance has been combined is immobilized onto a solid phase in accordance with the same manner as that described above, a blocking treatment is further applied to the solid phase, and then, the signal intensity thereof is measured. The protein used for the calibration curve may be, for example, globulin, actin or the like.

As compared with a manner for detecting a signal without immobilizing a blocking agent and a manner wherein a blocking agent is immobilized prior to immobilizing a complex onto a solid phase to detect a signal, such a manner as in the present embodiment wherein a blocking agent is further immobilized to a solid phase onto which a complex has been immobilized can reduce a background in case of detecting a signal. According to the latter manner of the present embodiment, the emission of the signal from the signal emitting substance, which has been adsorbed nonspecifically to the solid phase, can be effectively suppressed, while the signal from the complex cannot be substantially suppressed. As a result, a ratio (S/N ratio) of the signal emitted from the complex and the background based on the signal emitting substance, which has been adsorbed nonspecifically to the solid phase, may be improved. Thus, an analyte in a sample can be exactly detected.

In case of preparing a calibration curve, when a blocking agent is further immobilized to a solid phase onto which a complex has been immobilized, a gradient of the calibration curve can be increased as compared with that of a conventional manner, so that the resolution of the measurement value in case of detecting an analyte is improved. In other words, when the calibration curve prepared by applying a method of the present embodiment is used, a quantification of an analyte can be carried out more exactly.

In the case where an analyte is a substance produced by an enzymatic reaction, when the analyte is detected in accordance with the above-described method, it becomes possible to measure the activity of the enzyme. In the following, a method for measuring enzyme activity based on the detection of an analyte will be described.

An enzyme to be a target for activity measurement is not specifically limited, but kinases, peptidases, polymerases and the like are applicable. For instance, when activity of a kinase is measured, first, adenosine triphosphate (ATP), adenosine diphosphate (ADP), adenosine mono-phosphate (AMP) or the analogs thereof (e.g. ATPγS and the like), kinase, and a substrate are reacted with each other to introduce a phosphate group into the substrate. Then, a signal emitting substance which can combine with the phosphorylated substrate (hereinafter, referred to as "phosphorylated substrate"), but it is not combined substantially with a substrate, which has not been phosphorylated, is used to form a complex of the phosphorylated substrate and the signal emitting substance. The complex is immobilized to the solid phase, and a signal is detected in accordance with the above-mentioned method. Hence, a phosphorylated substrate is quantified dependent on the intensity of the signal to be detected. In the case where the activity of a kinase is high, the formation of the phosphorylated substrate is large, while when the activity of the kinase is low, the formation of the phosphorylated substrate is small. As a result, the activity of the kinase may be measured on the basis of the quantified result of the phosphorylated substrate. In this case, the phosphorylated substrate corresponds to the above-mentioned analyte.

A specific example of the kinases, which may be a target for measuring the activity, includes calcium/calmodulin-dependent proteinkinase (such as myosin L-chain kinase, eEF 2-kinase, and phosphorylase kinase), cyclic nucleotide regulated kinase, CDK (such as CDK1, CDK2, CDK3, CDK4, CDK5, CDK6, CDK7, and CDK8) and the like.

In case of measuring enzymatic activity, a sample containing an analyte is prepared by such a manner that a biological sample containing an enzyme is mixed with a substrate corresponding to the enzyme to conduct an enzymatic reaction. Dependent on an enzyme, there is a case where a further substance is required for the enzymatic reaction wherein the further substance may also be properly added. For instance, ATP, ADP, AMP or the analogs thereof is required to add to the mixture in case of measuring the activity of a kinase.

The biological sample containing an enzyme is not specifically limited as long as it is the one containing an enzyme as the one to be a target for measuring the activity. For instance, biological samples such as clumps of cells, blood, urine, and semen may be applied. In the case where the enzyme, which is a target to be measured, is contained in the inside of a cell, it is preferred that the cell membrane thereof is broken down to make it present in a free state in the sample. Moreover, in the case where the enzyme that is a target to be measured is contained in the inside of a nucleus, it is preferred that the nuclear membrane thereof is also broken down. For the purpose, it is preferred to conduct a solubilization treatment with respect to the biological sample prior to the reaction of the enzyme in the sample with a support. The solubilization treatment means that the cell membrane and the nucleus membrane contained in the cell in the sample are broken out physically and/or chemically, whereby the molecules existing inside the membranes are liberated.

The solubilization treatment is preferably implemented to add a buffer solution for solubilization treatment (hereinafter, referred to as "lysis buffer") to a biological sample. To the lysis buffer, a substance to inhibit a deactivation of an enzyme, a substance for breaking down a cell membrane or a nucleus membrane may be contained.

For example, a lysis buffer containing a buffer material is added to a sample; and by suction and discharge by a syringe, ultrasonic treatment, homogenization by a Waring blender etc, a solubilization treatment may be applied to the biological sample. A surfactant or a protease inhibitor may be contained into the lysis buffer. In the case where a target for measuring activity is a kinase, an inhibitor of dephosphorylation enzyme may be contained into a lysis buffer.

A surfactant exhibits an action for breaking down a cell membrane or a nucleus membrane. A type of the surfactant is not specifically restricted as long as the surfactant has the action as described above. In this respect, however, the surfactant must have a surface-active action of a degree wherein the enzyme as a target to be measured is not deactivated. An example of such surfactant as described above includes Nonidet P-40 (NP-40), TritonX-100 (registered trademark of Union Carbide Chemical and Plastics Co.), deoxycholic acid, CHAPS and the like. With respect to the lysis buffer, these surfactants may be used alone or in the combinations thereof. A concentration of the surfactant in a lysis buffer is preferably 1 w/v % or less.

A protease inhibitor is applied for the purpose of preventing a decomposition of an enzyme as a target to be measured with the protease contained in a cell. An example of the protease inhibitors includes metalloprotease inhibitors such as EDTA, and EGTA; serine protease inhibitors such as PMSF, trypsin inhibitor, and chymotrypsin; and cysteine protease inhibitors such as iodoacetamide, and E-64. Furthermore, there is another example such as a commercially available protease inhibitor cocktail (Sigma Co.). In a lysis buffer, these protease inhibitors may be used alone or in the combinations thereof.

A dephosphorylation enzyme inhibitor is used for the sake of preventing from decreasing activity of an enzyme as a target to be measured with the dephosphorylation enzyme contained in a cell. An example of the dephosphorylation enzyme inhibitor includes serine/threonine dephosphorylation enzyme inhibitors (sodium fluoride and the like), tyrosine dephosphorylation enzyme inhibitors (sodium orthovanadate and the like) and the like. In a lysis buffer, these dephosphorylation enzyme inhibitors may be alone or in the combinations thereof.

In the case where an enzyme as a target for measuring the activity is CDK1 or CDK2, it is preferred to use histone H1 or retinoblastoma protein (hereinafter referred simply to as "Rb") as the substrate. Furthermore, when an enzyme is CDK4 or CDK6, it is preferred to use Rb as the substrate. It is preferred that the substrate is made of a protein constituted from an amino acid containing no sulfur atom (the amino acids other than cysteine and methionine). It is preferred that the protein such as Rb containing a cysteine residue is used after substituting the cysteine residue by amino acids each containing no sulfur atom such as alanine and the like. As a manner for substituting cysteine or methionine in the substrate by the amino acids each containing no sulfur atom, a well-known method such as insertional mutagenesis to which a PCR method is applied may be used.

In the case where an enzyme as a target to be measured is a kinase, ATP, ADP, AMP or the analogs thereof are required for the reaction of the enzyme and a substrate as mentioned above. In the present embodiment, it is preferred to use ATPγS which corresponds to the one wherein a sulfur atom is combined with ATP. In this case, a thiophosphate group of the ATPγS is introduced into the substrate by the action of the kinase as mentioned above, and a signal emitting substance is combined with the thiophosphate group.

In the case where an enzyme as a target to be measured is a splitting enzyme, for example, a signal emitting substance comprising antibody which does not combine with a substrate prior to an enzyme reaction, but combines specifically with the product degraded by the enzyme may be applied.

The respective steps of the detection method of an analyte as well as the measuring method of enzyme activity thereof may be manually or automatically conducted by using equipment or the like.

EXAMPLE 1

A cell suspension was prepared by adding $2 \times 10^7$ cells of K562 (cultured cells derived from leukemia) to 1 ml of a lysis buffer (containing 0.1 w/v % of Nonidet P40 (NP40, Calbiochem), 50 mM of trishydrochloric acid (pH 7.4), 5 mM of EDTA, 50 mM of sodium fluoride, 1 mM of sodium orthovanadate, and 2 μl/ml of protease inhibitor cocktail (Sigma)).

By employing an electrically operated homogenizer, the cells in the cell suspension were homogenized, and the resulting homogenate was centrifugally separated in 15000 rpm at 4° C. for 5 minutes to obtain a supernatant fluid as a sample for measurement.

Five hundreds μl of a immunoprecipitation buffer solution (containing 0.1 v/v % of NP 40, and 50 mM of trishydrochloric acid (pH 7.4)) were contained in 1.5 ml Eppendorf tube; into which 20 μl of Sepharose beads (Amersham Co.) coated with 2 μg of anti-CDK2 antibody (Santa Cruz Co.) and protein A were added.

Then, a sample for measurement was added to each of the tubes wherein a concentration of the whole proteins in the tube was adjusted to be 25, 50, 75, and 100 μg/500 μl, respectively. On one hand, a tube wherein no sample for measurement was added and the whole protein mass thereof was 0 μg was also prepared.

These tubes were shaken at 4° C. for one hour to make a reaction of the CDK2 with the anti-CDK2 antibody. After the reaction, the beads in the tube were washed twice with a bead washing solution A (containing 1 v/v % of NP-40 and 50 mM of trishydrochloric acid (pH 7.0), washed once with a bead washing solution B (containing 300 mM of NaCl, and 50 mM of trishydrochloric acid (pH 7.4)), and washed once with a bead washing solution C (containing 50 mM of trishydrochloric acid (pH 7.4)).

Next, a substrate solution of CDK (containing 10 μg of histone H1 (Upstate Biotechnology Co.), 2 mM of ATP-γS (Sigma Co.), 40 mM of trishydrochloric acid (pH 7.4), 20 mM of $MgCl_2$, and 0.1% of Triton X-100) was added. The substrate solution was adjusted in such that a total amount of the mixed solution contained in the tube becomes 50 μl, and then, it was added. The resulting mixture was shaken at 37° C. for 30 minutes to conduct a kinase reaction, whereby a thiophosphate group was introduced into the histone H1.

After the kinase reaction, the beads were settled down by means of centrifugal separation in 2000 rpm for 20 seconds to collect 18 μl of a supernatant fluid.

To the supernatant fluid, 15 μl of a combination buffer solution (containing 150 mM of trishydrochloric acid (pH 7.4), and 5 mM of EDTA), and a 5IAF solution (containing 2.58 mM of 5IAF, 150 mM of trishydrochloric acid (pH 7.5), and 5 mM of EDTA) were added; and the resulting product was allowed to stand at a room temperature for 20 minutes in a dark place, whereby 5IAF is combined with the sulfur atom on the substrate into which a thiophosphate group was introduced (thiophosphorilated substrate).

Stoppage of the reaction of 5IAF and thiophosphate group was made by the addition of 2-mercaptoethanol as a reaction stopper.

A sample containing 0.35 μg of thiophosphorilated substrate with which 5IAF had been combined was blotted on a PVDF membrane by the use of a slot blotter.

The resulting PVDF membrane was washed six times with 200 μl of a membrane washing solution (containing 25 mM of trishydrochloric acid (pH 7.4), and 150 mM of NaCl).

After the washing, a blocking solution for decreasing background (containing 4 w/v % of BSA, 25 mM of trishydrochloric acid (pH 7.4), and 150 mM of NaCl) was further blotted onto the PVDF membrane.

Thereafter, a fluorescent analysis of the PVDF membrane was conducted by using a fluorescent image analyzer "Molecular Imager FX" (Bio-Rad Co.) to measure the fluorescence intensity. The fluorescence intensity is indicated as a fluorescence count value (unit=CNT).

COMPARATIVE EXAMPLES 1 TO 3

In comparative example 1, the fluorescence intensity was measured in accordance with the same manner as that of example 1 except that the Sepharose beads coated with the anti-CDK2 antibody were not used, but the Sepharose beads, which had not been coated with the anti-CDK2 antibody, were used.

In comparative example 2, the fluorescence intensity was measured in accordance with the same manner as that of example 1 except that the blocking solution was not used.

In comparative example 3, the fluorescence intensity was measured in accordance with the same manner as that of comparative example 1 except that the blocking solution was not used.

(Results)

Figure 2:
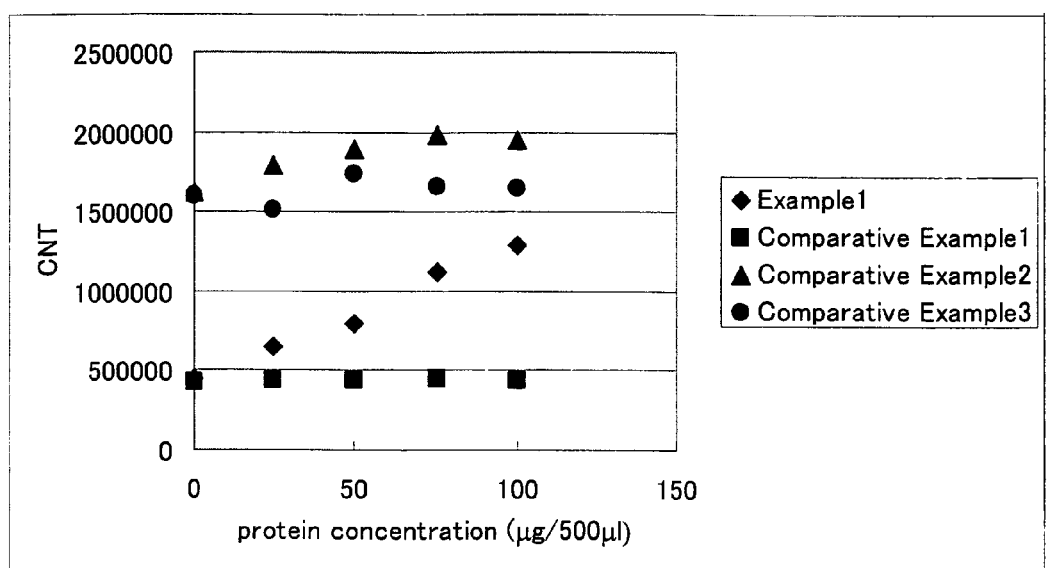
FIG. 2 shows a graph of fluorescent intensity measured in Example 1, Comparative example 1, Comparative example 2, and Comparative example 3.

The photographs of the PVDF membranes of example 1 and comparative examples 1 to 3 are shown in FIG. 1. Furthermore, a graph of the fluorescence intensities measured in example 1 and comparative examples 1 to 3 is shown in FIG. 2 wherein the fluorescence intensities are indicated as fluorescence count values (CNT).

From FIG. 1, it has been found that when the blocking treatment is applied (example 1 and comparative example 1) after the complex of the thiophosphorilated substrate (analyte) and 5IAF (signal emitting substance) was immobilized, the backgrounds can be reduced as compared with that of the case where no blocking treatment is conducted (comparative examples 2 and 3). On one hand, it has been found from FIG. 2 that when the blocking treatment is applied, a ratio of the signal (a value obtained by subtracting the background value from the signal of example 1) and the background value (S/N ratio) is improved as compared with that of the case where no blocking treatment is conducted. In addition, a fluorescence count value increases dependent on a protein concentration in only the graph of example 1, and it indicates the better linearity. From the above description, it has been confirmed that thiophosphorilated histone H1 can be quantified exactly in accordance with the manner of example 1.

A calibration curve for calculating the activity of CDK2 may be obtained as described below. First, a solution containing a protein (e.g. globulin and the like) having a known concentration and labeled with 5IAF is blotted on a PVDF membrane. Further, a blotting agent is blotted thereto. Then, the fluorescence intensity of the protein blotted on the PVDF membrane is measured by means of a fluorescence image analyzer to prepare the calibration curve. When the fluorescence count value to be measured in example 1 is applied to the calibration curve, the activity of the CDK2 contained in a sample can be calculated.

EXAMPLE 2

In example 2, a fluorescence intensity was measured in accordance with the same manner as that of example 1 except that 5IAF was not used as the signal emitting substance, but OGI was used, and that 2-mercaptoethanol was not used as the reaction stopper, but L-type cysteine was used.

COMPARATIVE EXAMPLES 4 TO 6

In comparative example 4, a fluorescence intensity was measured in accordance with the same manner as that of comparative example 1 except that 5IAF was not used as the signal emitting substance, but OGI was used, and that 2-mercaptoethanol was not used as the reaction stopper, but L-type cysteine was used.

In comparative example 5, a fluorescence intensity was measured in accordance with the same manner as that of comparative example 2 except that 5IAF was not used as the signal emitting substance, but OGI was used, and that 2-mercaptoethanol was not used as the reaction stopper, but L-type cysteine was used.

In comparative example 6, a fluorescence intensity was measured in accordance with the same manner as that of comparative example 3 except that 5IAF was not used as the signal emitting substance, but OGI was used, and that 2-mercaptoethanol was not used as the reaction stopper, but L-type cysteine was used.

(Results)

Figure 3:
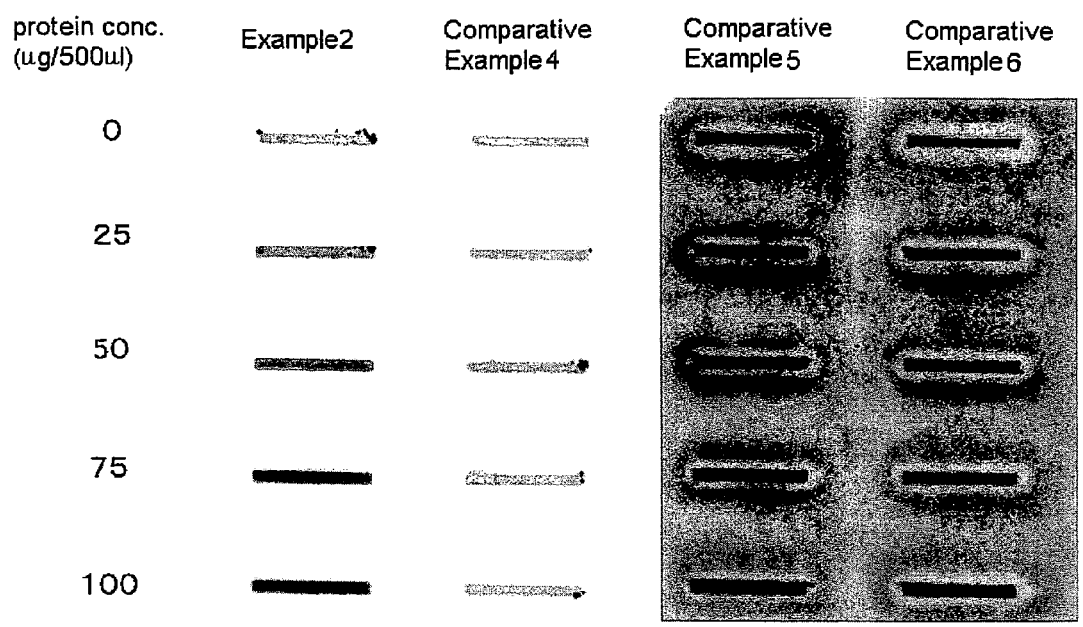
FIG. 3 shows a photograph of PVDF membrane of Example 2, Comparative example 4, Comparative example 5, and Comparative example 6.
Figure 4:
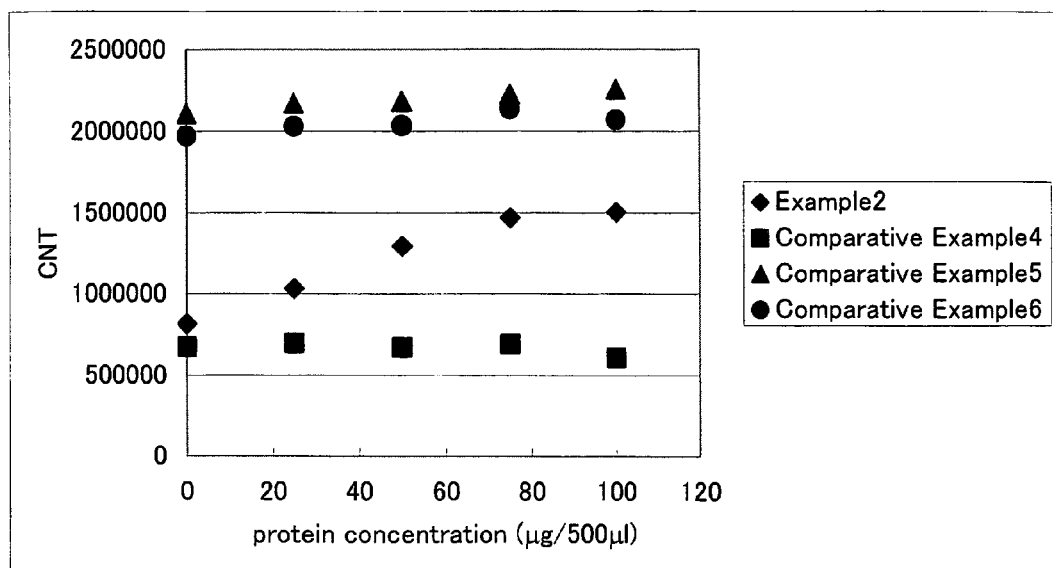
FIG. 4 a graph of fluorescent intensity measured in Example 2, Comparative example 4, Comparative example 5, and Comparative example 6.

The photographs of the PVDF membranes of example 2 and comparative examples 4 to 6 are shown in FIG. 3. Furthermore, a graph of the fluorescence intensities measured in example 2 and comparative examples 4 to 6 is shown in FIG. 4.

From FIG. 3, it has been found that when the blocking treatment is applied (example 2 and comparative example 4) after the complex of the thiophosphorilated substrate (analyte) and OGI (signal emitting substance) was immobilized, the backgrounds can be reduced as compared with that of the case where no blocking treatment is conducted (comparative examples 5 and 6). On one hand, it has been found from FIG. 4 that when the blocking treatment is applied, a ratio of the signal (a value obtained by subtracting the background value from the signal of example 1) and the background value (S/N ratio) is improved as compared with that of the case where no blocking treatment is conducted. In addition, a fluorescence count value increases dependent on a protein concentration in only the graph of example 2, and it indicates the better linearity. From the above description, it has been confirmed that thiophosphorilated histone H1 can be quantified exactly in accordance with the manner of example 2.

The activity of an enzyme can be calculated by such method as described hereinafter that a calibration curve is prepared in accordance with the same manner as that mentioned above except that the protein labeled with 5IAF is not used, but a protein labeled with OGI is used, and the fluorescence count value to be measured in example 2 is applied to the calibration curve.

EXAMPLE 3

A fluorescence intensity was measured in accordance with the same manner as that of example 1.

COMPARATIVE EXAMPLES 7 TO 9

In comparative example 7, a fluorescence intensity was measured in accordance with the same manner as that of comparative example 1.

In comparative example 8, the fluorescence intensity of histone H1 labeled with FITC was measured in accordance with the same manner as that of example 1 except that 5IAF was not used as the signal emitting substance, but StreptAvidin-FITC (Vector Co.) was used, that the blocking agent was not blotted after the complex had been blotted, but Iodoacetyl Biotin was combined with histone H1, the resulting product was blotted, and then, a blocking agent was blotted, and that StreptAvidin-FITC was blotted after the blocking agent had been blotted, whereby a fluorescence labeling was implemented with respect to a substrate.

In comparative example 9, a fluorescence intensity was measured in accordance the same manner as that of comparative example 8 except that an anti-CDK2 antibody was not used.

(Results)

Figure 5:
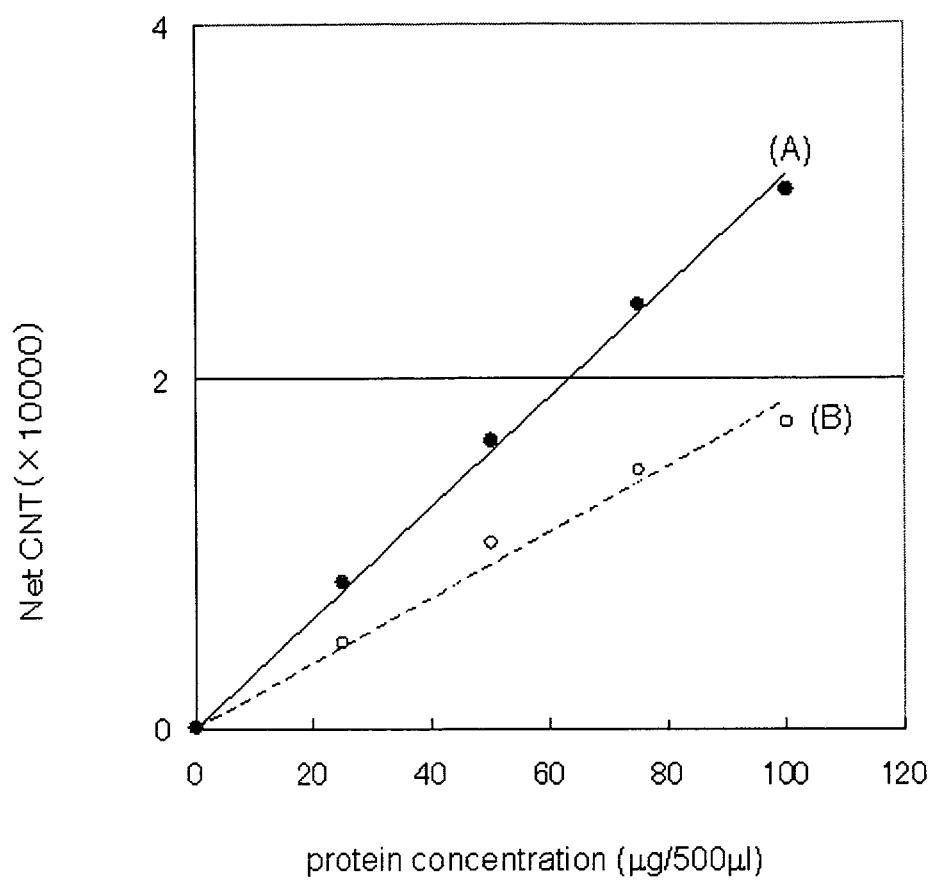
FIG. 5 shows graphs (A) and (B)

A graphical representation (A) indicating a value obtained by subtracting the fluorescence count value measured in comparative example 7 from the fluorescence count value measured in example 3, and a graphical representation (B) indicating a value obtained by subtracting the fluorescence count value measured in comparative example 9 from the fluorescence count value measured in comparative example 8 are shown in FIG. 5 wherein the axes of ordinate in the graphical representations (A) and (B) indicate values of the signals in example 3 and comparative example 8, and they are represented by Net CNT.

From FIG. 5, it has been found that the graphical representations (A) and (B) indicate a good linearity dependent on protein concentration, respectively, but a gradient in the graphical representation (A) is larger than that of the graphical representation (B). Accordingly, when a calibration curve in case of measuring an enzyme activity is prepared in accordance with the same manner as that of example 3, such calibration curve having a larger gradient than that of the conventional one can be obtained. When the calibration curve having such a larger gradient as described above is applied, the resolution of measured values is improved. In other words, when an enzyme activity is measured based on the calibration curve prepared in accordance with the manner of the present examples, the activity can be calculated more exactly than that obtained heretofore.

EXAMPLE 4

A fluorescence intensity was measured in accordance with the same manner as that of example 1 except that 500 µl of the immunoprecipitation buffer solution were not contained in 1.5 ml Eppendorf tube, but 150 µl of the buffer solution were contained, that the sample for measurement was added to each of the tubes wherein a concentration of the proteins in the tube was not adjusted to be 25, 50, 75, and 100 µg/500 µl, respectively, but to be 10 µg/150 µl, and 25 µg/150 µl, and that the Sepharose beads coated with 2 µg of anti-CDK2 antibody was not used, but the Sepharose beads coated with 4 µg of anti-CDK1 antibody (Santa Cruz Co.) was used.

COMPARATIVE EXAMPLES 10 TO 12

In comparative example 10, a fluorescence intensity was measured in accordance with the same manner as that of example 4 except that the anti-CDK1 antibody was not used.

In comparative example 11, the fluorescence intensity of histone H1 labeled with FITC was measured in accordance with the same manner as that of example 4 except that 5IAF was not used as the signal emitting substance, but StreptAvidin-FITC (Vector Co.) was used, that the blocking agent was not blotted after the labeled histone H1 had been blotted, but Iodoacetyl Biotin was combined with histone H1, the resulting product was blotted, and then, a blocking agent was blotted, and that StreptAvidin-FITC was blotted after the blocking agent had been blotted, whereby a fluorescence labeling operation was implemented with respect to a substrate.

In comparative example 12, a fluorescence intensity was measured in accordance the same manner as that of comparative example 11 except that an anti-CDK1 antibody was not used.

(Results)

Figure 6:
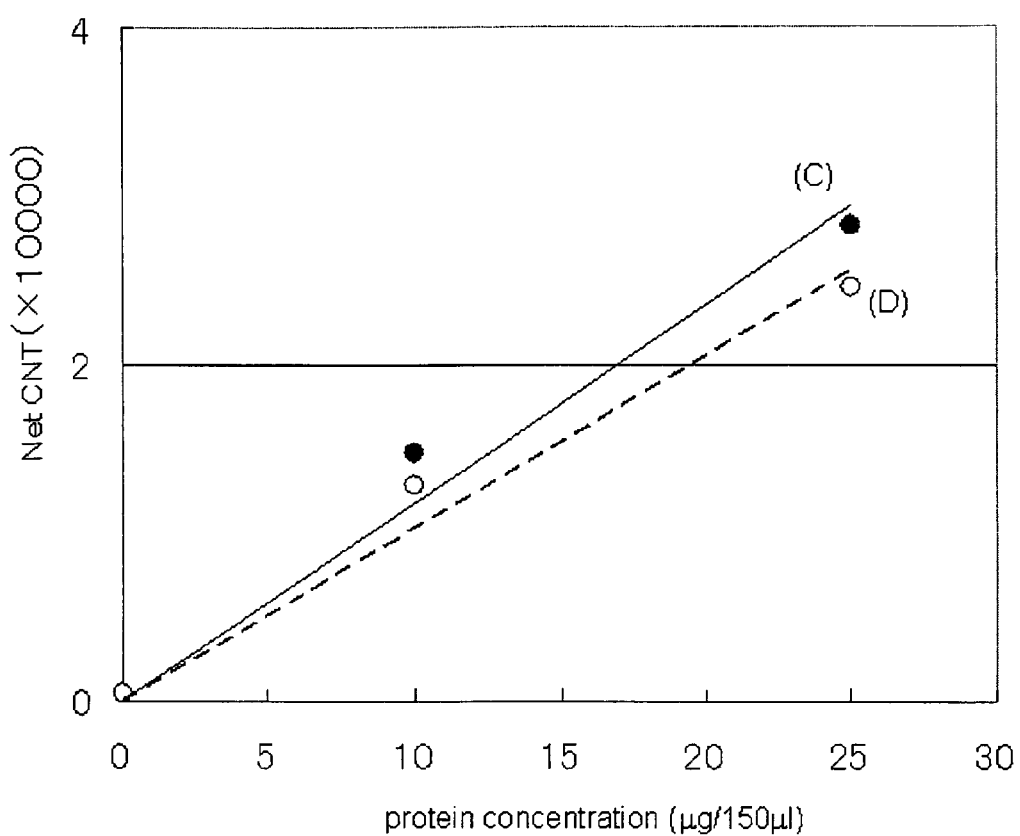
FIG. 6 shows graphs (C) and (D)

A graphical representation (C) indicating a value obtained by subtracting the fluorescence count value measured in comparative example 10 from the fluorescence count value measured in example 4, and a graphical representation (D) indicating a value obtained by subtracting the fluorescence count value measured in comparative example 12 from the fluorescence count value measured in comparative example 11 are shown in FIG. 6 wherein the axes of ordinate in the graphical representations (C) and (D) indicate values of the signals in example 4 and comparative example 11, and they are represented by Net CNT.

From FIG. 6, it has been found that the graphical representations (C) and (D) indicate a good linearity dependent on protein concentration, respectively, but a gradient in the graphical representation (C) is larger than that of the graphical representation (D). Accordingly, when a calibration curve in case of measuring an enzyme activity is prepared in accordance with the same manner as that of example 3, such calibration curve having a larger gradient than that of the conventional one can be obtained. When the calibration curve having such a larger gradient as described above is applied, the resolution of measured values is improved. In other words, when an enzyme activity is measured based on the calibration curve prepared in accordance with the manner of the present examples, the activity can be calculated more exactly than that in the prior art.

EXAMPLE 5

A fluorescence intensity was measured in accordance with the same manner as that of example 1 except that 500 µl of the immunoprecipitation buffer solution were not contained in 1.5 ml Eppendorf tube, but 1000 µl of the buffer solution were contained, that the sample for measurement was added to each of the tubes wherein a concentration of the proteins in the tube was not adjusted to be 25, 50, 75, and 100 µg/500 µl, respectively, but to be 25, 50, and 75 µg/1000 µl, and that the blocking solution which did not contain 4 w/v % of BSA, but contain 1 w/v % of casein was used.

COMPARATIVE EXAMPLE 13

In comparative example 13, a fluorescence intensity was measured in accordance with the same manner as that of example 5 except that the Sepharose beads which had not been coated with the anti-CDK2 antibody were used.

(Results)

Figure 7:
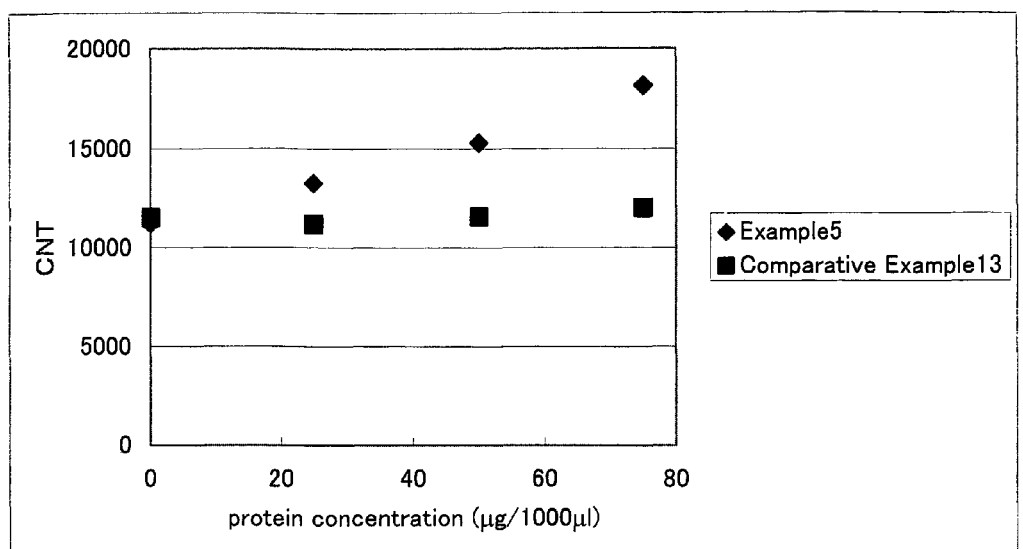
FIG. 7 shows a graph of fluorescent intensity measured in Example 5, and Comparative example 13.

The graphical representations of the fluorescence intensities measured in example 5 and comparative example 13 were shown in FIG. 7.

From FIG. 7, it has been found that the fluorescence count value increases dependent on a protein concentration, and further it indicates the better linearity. Accordingly, it has been confirmed that not only the BSA is used as the blocking agent, but also casein may be used.

EXAMPLE 6

A fluorescence intensity was measured in accordance with the same manner as that of example 1 except that a substrate solution containing 10 µg of histone H1 was not used, but 10 µg of Rb were used, and that the sample for measurement was added to each of the tubes wherein a concentration of the proteins in the tube was not adjusted to be 25, 50, 75, and 100 µg/500 µl, respectively, but to be 37.5, and 75 µg/500 µl.

COMPARATIVE EXAMPLE 14

In comparative example 14, a fluorescence intensity was measured in accordance with the same manner as that of example 6 except that the Sepharose beads which had not been coated with the anti-CDK2 antibody were used.

(Results)

Figure 8:
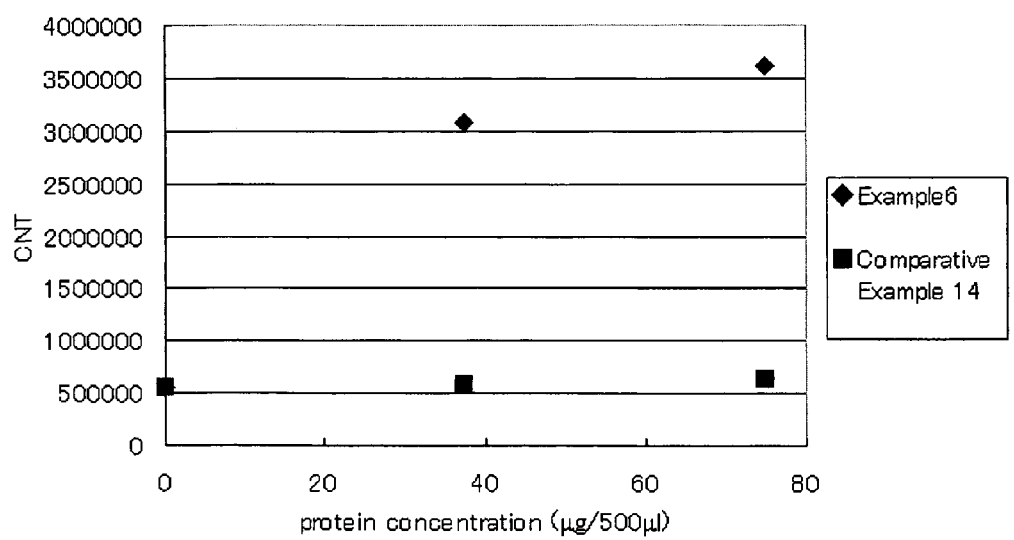
FIG. 8 shows a graph of fluorescent intensity measured in Example 6, and Comparative example 14.

The graphical representations of the fluorescence intensities measured in example 6 and comparative example 14 were shown in FIG. 8.

From FIG. 8, it has been found that the fluorescence count value increases dependent on a protein concentration, and further it indicates the better linearity. Accordingly, it has been confirmed that not only the histone H1 is used as the substrate, but also Rb may be used.

EXAMPLE 7

A fluorescence intensity was measured in accordance with the same manner as that of example 1 except that 2-mercaptoethanol was not used as the reaction stopper, but L-type cysteine was used.

COMPARATIVE EXAMPLES 15 TO 17

Fluorescence intensities were measured in accordance with the same manner as that of comparative examples 1 to 3, respectively, except that 2-mercaptoethanol was not used as the reaction stopper, but L-type cysteine was used in each case.

(Results)

Figure 9:
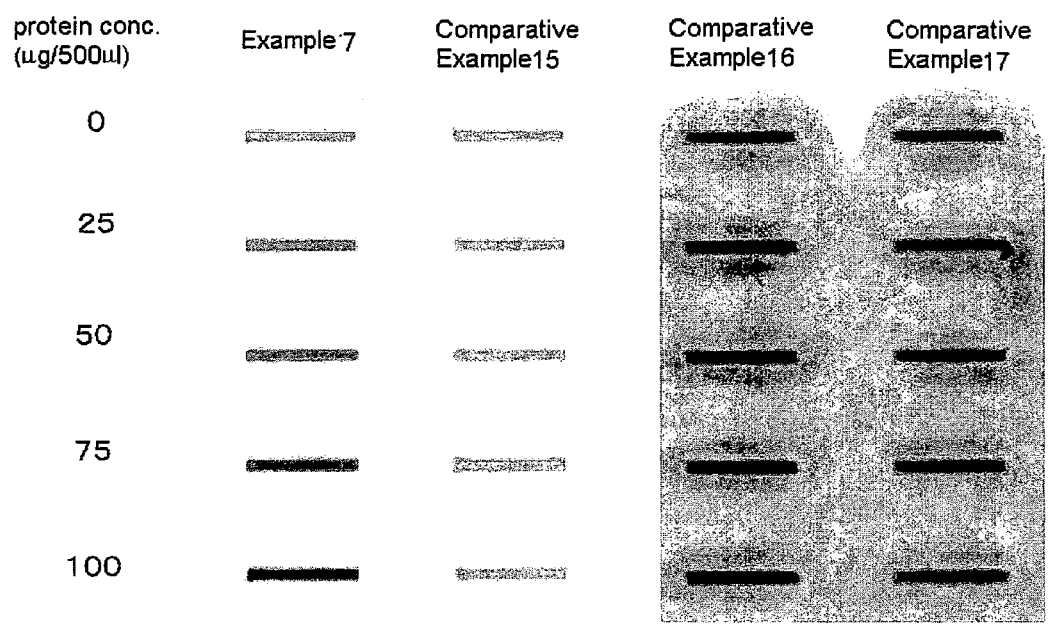
FIG. 9 shows a photograph of PVDF membrane of Example 7, Comparative example 15, Comparative example 16, and Comparative example 17.

The photographs of the PVDF membranes of example 7 and comparative examples 15 to 17 are shown in FIG. 9. Furthermore, a graph of the fluorescence intensities measured in example 7 and comparative examples 15 to 17 is shown in FIG. 10 wherein the fluorescence intensities are indicated as fluorescence count values (CNT).

Figure 10:
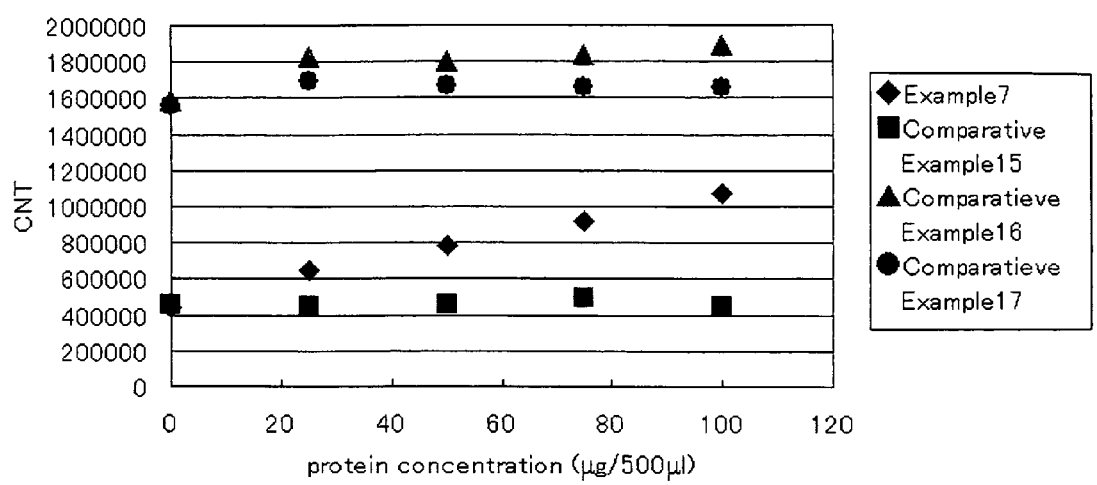
FIG. 10 shows a graph of fluorescent intensity measured in Example 7, Comparative example 15, Comparative example 16, and Comparative example 17.

From FIGS. 9 and 10, it has been confirmed that histone H1 can be exactly quantified as in the case of example 1, although L-type cysteine is used as the reaction stopper in example 7.

The activity of an enzyme can be calculated by such a manner that a calibration curve is prepared in accordance with the same manner as that mentioned above, and the fluorescence count value to be measured in example 7 is applied to the calibration curve.

EXAMPLE 8

In example 8, a fluorescence intensity was measured in accordance with the same manner as that of example 2 except that the L-type cysteine was not used as the reaction stopper, but 2-aminoethanethiol was used.

COMPARATIVE EXAMPLES 18 TO 20

In comparative examples 18 to 20, fluorescence intensities were measured in accordance with the same manner as that of comparative examples 4 to 6, respectively, except that the L-type cysteine was not used as the reaction stopper, but 2-aminoethanethiol was used in each case.

(Results)

Figure 11:
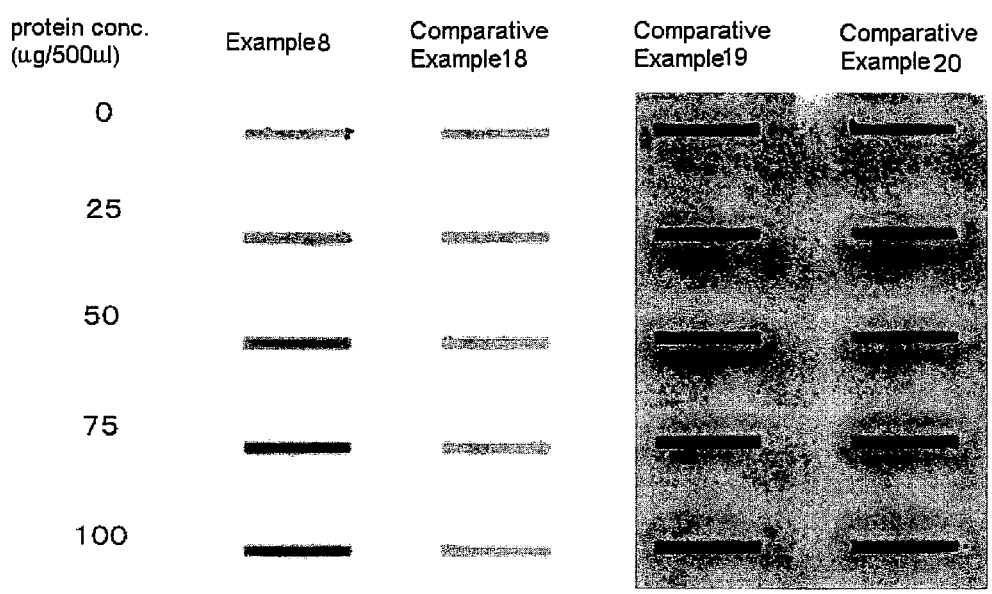
FIG. 11 shows a photograph of PVDF membrane of Example 8, Comparative example 18, Comparative example 19, and Comparative example 20.
Figure 12:
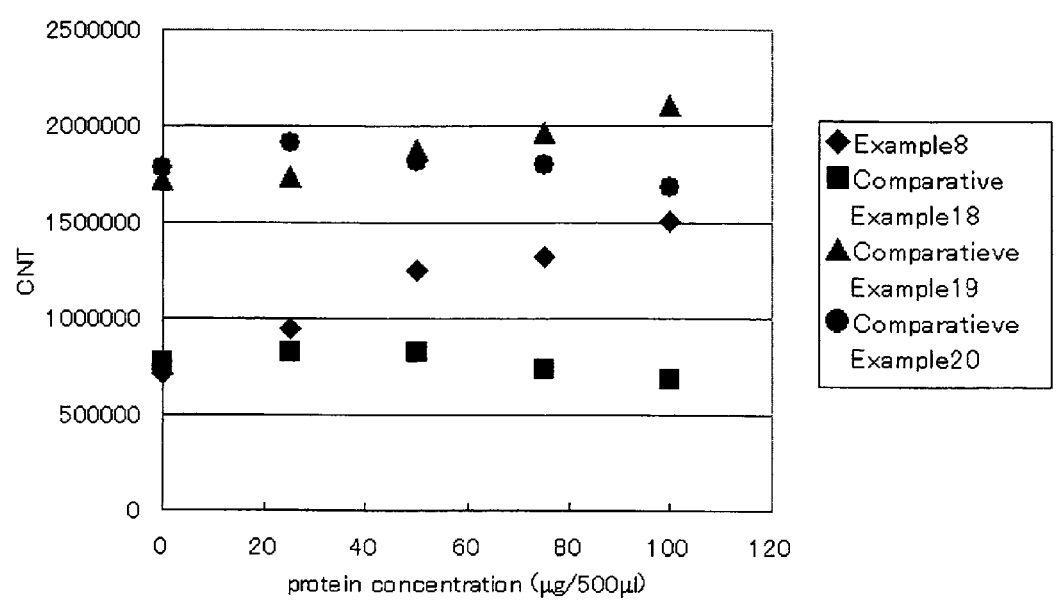
FIG. 12 shows a graph of fluorescent intensity measured in Example 8, Comparative example 18, Comparative example 19, and Comparative example 20.

The photographs of the PVDF membranes of example 8 and comparative examples 18 to 20 are shown in FIG. 11. Furthermore, a graph of the fluorescence intensities measured in example 8 and comparative examples 18 to 20 is shown in FIG. 12.

From FIGS. 9 and 10, it has been confirmed that histone H1 can be exactly quantified as in the case of example 2, although 2-aminoethanethiol is used as the reaction stopper in example 8.

The activity of an enzyme can be calculated by such a manner that a calibration curve is prepared in accordance with the same manner as that mentioned above, and the fluorescence count value to be measured in example 2 is applied to the calibration curve.

EXAMPLES 9 AND 10

In example 9, a fluorescence intensity was measured in accordance with the same manner as that of example 1 except that the 2-mercaptoethanol was not used as the reaction stopper, but acetylcysteine was used.

In example 10, a fluorescence intensity was measured in accordance with the same manner as that of example 1.

COMPARATIVE EXAMPLES 21 AND 22

In comparative example 21, a fluorescence intensity was measured in accordance with the same manner as that of comparative example 1 except that the 2-mercaptoethanol was not used as the reaction stopper, but acetylcysteine was used.

In comparative example 22, a fluorescence intensity was measured in accordance with the same manner as that of comparative example 1.

(Results)

Figure 13:
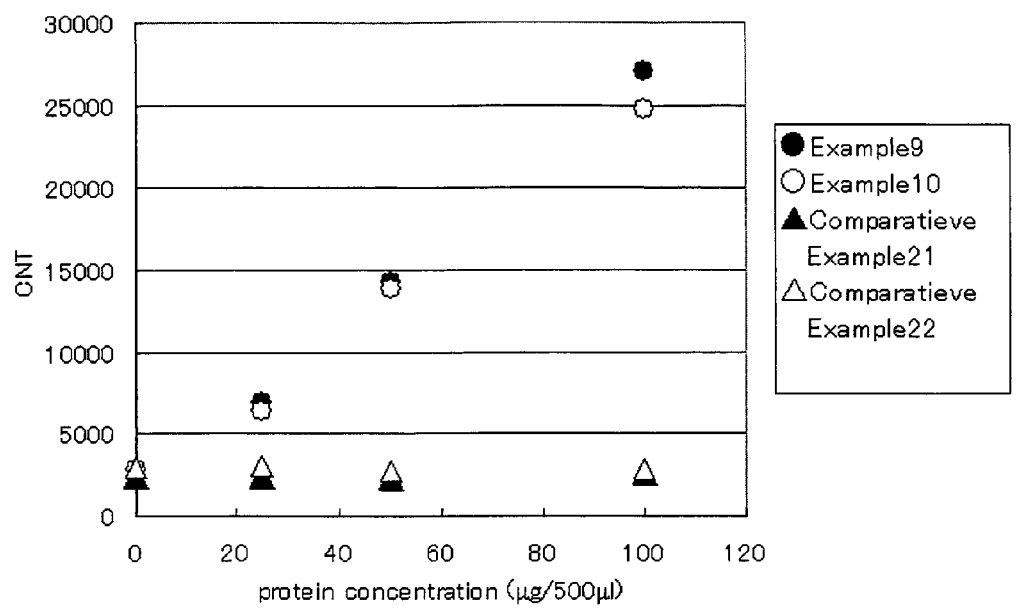
FIG. 13 shows a graph of fluorescent intensity measured in Example 9, Example 10, Comparative example 21, and Comparative example 22.

The graphs of the fluorescence intensities measured in examples 9 and 10 as well as comparative examples 21 and 22 are shown in FIG. 13.

From FIG. 13, it has been found that the fluorescence count value increases dependent on a protein concentration in the graph of example 9 wherein acetylcysteine is used as the reaction stopper as in the case of example 10, and it indicates the better linearity. Accordingly, it has been confirmed that acetylcysteine may be used as the reaction stopper.

What is claimed is:

1. A method for detecting a protein in a sample, comprising the steps of:
    contacting a sample comprising a first protein with a fluorescent substance, whereupon said contacting, some of said fluorescent substance binds to said first protein in a binding reaction to form complexes, and some of said fluorescent substance remains unbound to said first protein;
    immobilizing said complexes and said unbound fluorescent substance to a solid substrate; and
    treating the solid substrate in which said complexes and said unbound fluorescent substance are immobilized thereon with a blocking protein, wherein said blocking protein selectively suppresses fluorescence from the unbound fluorescent substance without suppressing fluorescence from the fluorescent substance of said complexes; and
    exciting fluorescence from the fluorescent substance with excitation light, determining the amount of fluorescence produced, and quantifying the amount of said first protein in said sample based on said amount of fluorescence produced.

2. The method according to claim 1, wherein the blocking protein is selected from the group consisting of an albumin, a casein, a globulin, and a gelatin.

3. The method according to claim 1, wherein the solid substrate comprises a substrate selected from the group consisting of a polyvinylidene fluoride, a nitrocellulose, a cellulose acetate, and a nylon.

4. The method according to claim 1, wherein said binding reaction is stopped before said immobilization.

5. The method according to claim 4, wherein the step of stopping said binding reaction comprises adding a reducing agent having a thiol group.

6. The method according to claim 5, wherein the reducing agent is selected from the group consisting of a 2-mercaptoethanol, a D-cysteine, an L-cysteine, an acetylcysteine, a 2-mercaptopropionic acid, a mercaptoacetic acid, a 2-aminoethanethiol, a dithiothreitol, a glutathione, and a dodecanethiol.

7. The method according to claim 1, wherein the treating step comprises allowing said blocking protein to bind to the solid substrate in which said complex and said unbound fluorescent substance are immobilized thereon.

8. A method for quantifying a kinase activity in a sample, comprising the steps of:
    contacting a sample with a fluorescent substance, wherein said sample comprises a product of an enzymatic reaction between a kinase and a protein substrate for said kinase, whereupon said contacting, some of said fluorescent substance binds to said product in a binding reaction to form complexes, and some of said fluorescent substance remains unbound to said product;
    immobilizing said complexes and said unbound fluorescent substance onto a solid substrate; and
    treating the solid substrate in which said complexes and said unbound fluorescent substance are immobilized thereon with a blocking protein, wherein said blocking protein selectively suppresses fluorescence from the unbound fluorescent substance without suppressing fluorescence from the fluorescent substance of said complexes; and
    exciting fluorescence from the fluorescent substance with excitation light, determining the amount of fluorescence produced, and quantifying the activity of said kinase in said sample based on said amount of fluorescence produced.

9. The method according to claim 8, wherein the protein substrate is selected from the group consisting of a histone H1 and a Retinoblastoma protein.

10. The method according to claim 9, wherein cysteine residues of the Retinoblastoma protein are substituted by amino acids not comprising a sulfur atom.

11. The method according to claim 8, wherein the binding reaction comprises introducing a thiophosphate group into the protein substrate by using an adenosine-5'-O-(3-thiotriphosphate).

12. The method according to claim 11, wherein the fluorescent substance conjugates to the thiophosphate group introduced into said protein substrate.

* * * * *